United States Patent
Laufer et al.

(10) Patent No.: US 7,153,314 B2
(45) Date of Patent: Dec. 26, 2006

(54) TISSUE RECONFIGURATION

(75) Inventors: Michael D. Laufer, Menlo Park, CA (US); Jeffrey C. Cerier, Franklin, MA (US); Amos G. Cruz, Franklin, MA (US)

(73) Assignee: NDO Surgical, Mansfield, MA (US)

(*) Notice: Subject to any disclaimer, the term of this patent is extended or adjusted under 35 U.S.C. 154(b) by 324 days.

(21) Appl. No.: 10/219,258

(22) Filed: Aug. 16, 2002

(65) Prior Publication Data

US 2002/0193816 A1 Dec. 19, 2002

Related U.S. Application Data

(63) Continuation of application No. 09/574,424, filed on May 19, 2000, now Pat. No. 6,494,888, which is a continuation-in-part of application No. 09/520,273, filed on Mar. 7, 2000, now Pat. No. 6,663,639, and a continuation-in-part of application No. 09/519,945, filed on Mar. 7, 2000, now Pat. No. 6,506,196.

(60) Provisional application No. 60/140,492, filed on Jun. 22, 1999.

(51) Int. Cl.
*A61B 17/08* (2006.01)
*A61B 17/04* (2006.01)
*A61B 19/00* (2006.01)

(52) U.S. Cl. .................. 606/153; 606/139; 128/898

(58) Field of Classification Search ................ 606/153, 606/219, 220, 221, 232, 144, 148, 150, 151; 227/175.1; 600/104; 128/898
See application file for complete search history.

(56) References Cited

U.S. PATENT DOCUMENTS 3,470,875 A 10/1969 Johnson (Continued)

FOREIGN PATENT DOCUMENTS

EP 0 480 428 A2 4/1992

(Continued)

OTHER PUBLICATIONS

Bancewicz et al., "Yield pressure, anatomy of the cardia and gastro-oesophageal reflux", British Journal of Surgery, 1995, vol. 82, No. 7p. 943-947.

(Continued)

*Primary Examiner*—Julian W. Woo
(74) *Attorney, Agent, or Firm*—Morgan Lewis & Bockius LLP

(57) ABSTRACT

An apparatus includes an elongated member configured for transoral placement into a stomach, and a distal end effector including first and second members configured to engage stomach tissue, e.g., tissue beyond the esophageal junction. The first and second members are movable relatively toward one another generally in a first plane, and the distal end effector is movable relative to the elongated member in a second plane generally transverse to the first plane. A third member of the distal end effector is configured to engage stomach tissue. The third member is movable in a distal direction relative to the first and second members. A tissue securement member of the apparatus is coupled to at least one of the first and second members for securing together tissue engaged thereby. The tissue securement member includes first and second parts, a suture attached to the first part, and a securing element attached to the suture and configured for engagement with the second part when the first and second members move relatively toward one another to engage tissue, to thereby secure the second part to the first part.

16 Claims, 10 Drawing Sheets

U.S. PATENT DOCUMENTS

| | | |
|---|---|---|
| 3,551,987 A | 1/1971 | Wilinson |
| 3,638,653 A | 2/1972 | Berry |
| 3,749,085 A | 7/1973 | Willson et al. |
| 3,842,840 A | 10/1974 | Schweizer |
| 3,875,648 A | 4/1975 | Bone |
| 3,901,244 A | 8/1975 | Schweizer |
| 3,946,740 A | 3/1976 | Bassett |
| 4,006,747 A | 2/1977 | Kronenthal et al. |
| 4,164,225 A | 8/1979 | Johnson et al. |
| 4,235,238 A | 11/1980 | Ogiu et al. |
| 4,448,194 A | 5/1984 | DiGiovanni et al. |
| 4,471,781 A | 9/1984 | DiGiovanni et al. |
| 4,500,024 A | 2/1985 | DiGiovanni et al. |
| 4,506,670 A | 3/1985 | Crossley |
| 4,573,469 A | 3/1986 | Golden et al. |
| 4,585,153 A | 4/1986 | Failla et al. |
| 4,586,502 A | 5/1986 | Bedi et al. |
| 4,591,085 A | 5/1986 | Di Giovanni et al. |
| 4,605,004 A | 8/1986 | Di Giovanni et al. |
| 4,606,345 A | 8/1986 | Dorband et al. |
| 4,627,437 A | 12/1986 | Bedi et al. |
| 4,653,496 A | 3/1987 | Bundy et al. |
| 4,669,473 A | 6/1987 | Richards et al. |
| 4,696,300 A | 9/1987 | Anderson |
| 4,705,040 A | 11/1987 | Mueller |
| 4,724,840 A | 2/1988 | McVay et al. |
| 4,736,746 A | 4/1988 | Anderson |
| 4,741,336 A | 5/1988 | Failla et al. |
| 4,753,469 A | 6/1988 | Hiscott |
| 4,809,695 A | 3/1989 | Gwathmey |
| 4,841,888 A | 6/1989 | Mills et al. |
| 4,887,612 A | 12/1989 | Esser et al. |
| 4,890,615 A | 1/1990 | Caspari et al. |
| 4,935,027 A | 6/1990 | Yoon |
| 5,015,249 A | 5/1991 | Nakao |
| 5,037,433 A | 8/1991 | Wilk et al. |
| 5,080,663 A | 1/1992 | Mills et al. |
| 5,088,979 A | 2/1992 | Filipi et al. ............... 604/26 |
| 5,147,373 A | 9/1992 | Ferzli |
| 5,222,963 A | 6/1993 | Brinkerhoff et al. |
| 5,254,126 A | 10/1993 | Filipi et al. ............... 606/146 |
| 5,336,263 A | 8/1994 | Ersek |
| 5,346,504 A | 9/1994 | Ortiz et al. ............... 606/192 |
| 5,354,311 A * | 10/1994 | Kambin et al. ............ 606/205 |
| 5,356,416 A | 10/1994 | Chu et al. |
| 5,358,508 A | 10/1994 | Cobb |
| 5,364,408 A | 11/1994 | Gordon |
| 5,395,030 A | 3/1995 | Kuramoto et al. |
| 5,403,326 A | 4/1995 | Harrison et al. ............ 606/139 |
| 5,433,721 A | 7/1995 | Hooven et al. |
| 5,441,507 A | 8/1995 | Wilk |
| 5,447,512 A | 9/1995 | Wilson et al. |
| 5,451,406 A | 9/1995 | Lawin |
| 5,465,894 A | 11/1995 | Clark et al. |
| 5,486,189 A | 1/1996 | Mudry et al. |
| 5,496,331 A | 3/1996 | Xu |
| 5,522,820 A | 6/1996 | Caspari et al. |
| 5,549,618 A | 8/1996 | Fleenor et al. |
| 5,558,665 A | 9/1996 | Kieturakis ............... 606/1 |
| 5,571,090 A | 11/1996 | Sherts |
| 5,571,116 A | 11/1996 | Bolanos et al. ............ 606/143 |
| 5,573,496 A | 11/1996 | McPherson et al. ........ 600/217 |
| 5,624,453 A | 4/1997 | Ahmed |
| 5,626,613 A | 5/1997 | Schmieding |
| 5,645,552 A | 7/1997 | Shertz |
| 5,662,683 A | 9/1997 | Kay |
| 5,665,096 A | 9/1997 | Yoon |
| 5,674,230 A | 10/1997 | Tovey |
| 5,676,674 A | 10/1997 | Bolanos et al. ............ 606/139 |
| 5,697,940 A | 12/1997 | Chu et al. |
| 5,722,421 A | 3/1998 | Francese et al. |
| 5,725,524 A | 3/1998 | Mulier et al. |
| 5,728,109 A | 3/1998 | Schulze et al. |
| 5,735,861 A | 4/1998 | Peifer et al. |
| 5,741,280 A | 4/1998 | Fleenor |
| 5,749,898 A | 5/1998 | Schulze et al. |
| 5,787,897 A | 8/1998 | Kieturakis ............... 128/898 |
| 5,792,153 A | 8/1998 | Swain et al. |
| 5,792,478 A | 8/1998 | Lawin |
| 5,797,927 A | 8/1998 | Yoon |
| 5,810,855 A | 9/1998 | Rayburn |
| 5,810,882 A | 9/1998 | Bolduc et al. ............. 606/213 |
| 5,814,054 A | 9/1998 | Kortenbach et al. |
| 5,826,776 A | 10/1998 | Schulze et al. |
| 5,846,254 A | 12/1998 | Schulze et al. |
| 5,853,409 A | 12/1998 | Swanson et al. |
| 5,855,311 A | 1/1999 | Hamblin et al. |
| 5,887,594 A | 3/1999 | LoCicero, III et al. ..... 128/898 |
| 5,893,592 A | 4/1999 | Schulze et al. |
| 5,897,562 A | 4/1999 | Bolanos et al. ............ 606/139 |
| 5,899,915 A | 5/1999 | Saadat |
| 5,901,895 A | 5/1999 | Heaton et al. |
| 5,958,444 A | 9/1999 | Wallace |
| 5,984,932 A | 11/1999 | Yoon |
| 5,993,466 A | 11/1999 | Yoon |
| 6,009,877 A | 1/2000 | Edwards |
| 6,051,003 A | 4/2000 | Chu et al. |
| 6,059,798 A | 5/2000 | Tolkoff |
| 6,067,990 A | 5/2000 | Kieturakis ............... 128/898 |
| 6,083,202 A | 7/2000 | Smith |
| 6,086,600 A | 7/2000 | Kortenbach |
| 6,086,603 A | 7/2000 | Termin et al. |
| 6,098,629 A | 8/2000 | Johnson |
| 6,113,609 A | 9/2000 | Adams |
| 6,129,761 A | 10/2000 | Hubbell |
| 6,152,935 A | 11/2000 | Kammerer |
| 6,159,146 A | 12/2000 | El Gazayerli |
| 6,179,840 B1 | 1/2001 | Bowman |
| 6,221,084 B1 | 4/2001 | Fleenor |
| 6,238,335 B1 | 5/2001 | Silverman et al. |
| 6,254,642 B1 | 7/2001 | Taylor |
| 6,258,064 B1 | 7/2001 | Smith et al. |
| 6,352,503 B1 | 3/2002 | Matsui et al. |
| 6,387,104 B1 | 5/2002 | Pugsley, Jr. et al. |
| 6,540,789 B1 | 4/2003 | Silverman et al. |
| 6,544,291 B1 | 4/2003 | Taylor |
| 6,544,503 B1 | 4/2003 | Vanderhoff et al. |
| 6,547,776 B1 | 4/2003 | Gaiser et al. |
| 6,548,501 B1 | 4/2003 | Hakkinen |
| 6,551,315 B1 | 4/2003 | Kortenbach et al. |
| 6,558,400 B1 | 5/2003 | Deem et al. |
| 6,558,429 B1 | 5/2003 | Taylor |
| 6,562,034 B1 | 5/2003 | Edwards et al. |
| 6,569,105 B1 | 5/2003 | Kortenbach et al. |
| 6,579,301 B1 | 6/2003 | Bales et al. |
| 6,589,238 B1 | 7/2003 | Edwards et al. |
| 6,591,137 B1 | 7/2003 | Fischell et al. |
| 6,591,838 B1 | 7/2003 | Durgin |
| 6,592,596 B1 | 7/2003 | Geitz |
| 6,595,909 B1 | 7/2003 | Silverman et al. |
| 6,595,910 B1 | 7/2003 | Silverman et al. |
| 6,604,004 B1 | 8/2003 | Zelickson et al. |
| 6,613,047 B1 | 9/2003 | Edwards |
| 6,645,201 B1 | 11/2003 | Utley et al. |
| 6,660,301 B1 | 12/2003 | Vogel et al. |
| 6,669,713 B1 | 12/2003 | Adams |
| 6,673,070 B1 | 1/2004 | Edwards et al. |
| 6,695,764 B1 | 2/2004 | Silverman et al. |
| 6,712,074 B1 | 3/2004 | Edwards et al. |
| 6,712,814 B1 | 3/2004 | Edwards et al. |
| 6,725,866 B1 | 4/2004 | Johnson et al. |
| 2001/0049537 A1 | 12/2001 | Kortenbach |
| 2001/0056282 A1 | 12/2001 | Sonnenschein |
| 2002/0010418 A1 | 1/2002 | Lary et al. |

| | | | |
|---|---|---|---|
| 2002/0082621 | A1 | 6/2002 | Schurr |
| 2003/0068326 | A1 | 4/2003 | Gevas et al. |
| 2003/0135206 | A1 | 7/2003 | Edwards et al. |
| 2003/0163029 | A1 | 8/2003 | Sonnenschein et al. |
| 2003/0167062 | A1 | 9/2003 | Gambale et al. |
| 2003/0195509 | A1 | 10/2003 | Edwards et al. |
| 2003/0199731 | A1 | 10/2003 | Silverman et al. |
| 2003/0208209 | A1 | 11/2003 | Gambale et al. |
| 2004/0059350 | A1 | 3/2004 | Gordon et al. |
| 2004/0082950 | A1 | 4/2004 | Edwards et al. |

FOREIGN PATENT DOCUMENTS

| | | |
|---|---|---|
| EP | 0 576 265 A2 | 12/1993 |
| EP | 0 646 356 A2 | 4/1995 |
| EP | 0 668 058 | 8/1995 |
| EP | 0 743 044 | 4/2003 |
| EP | 0 975 263 | 10/2003 |
| FR | 2 768 324 | 3/1999 |
| JP | 61-122852 | 6/1986 |
| WO | WO 99/00059 | 1/1999 |
| WO | WO 99/22649 | 5/1999 |
| WO | WO 99/60931 | 12/1999 |
| WO | 00/78229 | 12/2000 |
| WO | WO 00/35529 | 12/2000 |
| WO | WO 00/78227 | 12/2000 |
| WO | WO 00/78229 | 12/2000 |
| WO | WO 02/24080 | 3/2002 |
| WO | WO 02/076541 | 10/2002 |

OTHER PUBLICATIONS

Kraemer et al., "Laparosocpic Hill Repair", Gastrointestinal Endoscopy, vol. 40, No. 2, part 1, 1994, p. 155-159.
Singh et al., "Evaluation of the Endoscopic Suturing System in the Treatment of the GERD", Conference Abstract for Plenary Session for Digestive Disease Week, p. 314 & A-802, May 16-19, 1999.
The American Journal of Gastroenterology, vol. 91, No. 3, 1996, p. 616-617.
European Search Report mailed Sep. 2, 2004 in EP Application No. 04 07 6389.
Boerema, M.D. , "Hiatus hernia: Repair by right-sided, subhepatic, anterior gastropexy," *Surgery*, 65:884-893 (1969).
Cecconello, "Esophagogastric Anastomosis with Valvuloplasty: An Experimental Study," *International Surgery*, 67:121-124 (1982).
Collis, M. D., "Surgical Control of Reflux in Hiatus Hernia," *The American Journal of Surgery*, 115:465-471 (1968).
Collis, M.D., "An Operation for Hiatus Hernia with Short Esophagus," *The Journal of Thoracic Surgery*, 34:768-778 (1957).
Cuschieri, et al. , "Multicenter prospective evaluation of laparoscopic antireflux surgery," *Surgical Endoscopy*, 7:505-510 (1993).
DeMeester, M.D. et al., "Nissen Fundoplication for Gastroesophageal Reflux Disease," *Annals of Surgery*, 204:9-20 (1986).
Donahue, M.D., et al., "Endoscopic Control of Gastro-Esophageal Reflux: Status Report," *World Journal of Surgery*, 16:343-346 (1992).
Donahue, M.D., et al., "Endoscopic sclerosis of the gastic cardia for prevention of experimental gastroesophageal reflux," *Gastrointestinal Endoscopy*, 36:253-256 (1990).
Falk, et al., "Laparoscopic Fundoplication: A preliminary report of the technique and postoperative care," *Aust. N.Z. J. Surgery*, 62:969-972 (1992).
Hill, et al., "*Surgery for Peptic Esophageal Stricture*," 139-147.
Hill, M.D., "An Effective Operation for Hiatal Hernia: An Eight Year Appraisal," *Annals of Surgery*, 166:681-692 (1967).
Hill, et al., "The Esophagus, Medical and Surgicial Management," *WB Saunders Co.*, 135-8 (1988).
Hinder, et al. "The Surgical Option for Gastroesophageal Reflux Disease," Symposium on Gastroesophageal Reflux Disease, *Am J Med*, 103:144S-148S (1997).
Ismail, et al., "Yield Pressure: A New Concept in the Evaluation of Gerd?," *AJG*, 91:616-617 (1996).

Jamieson, et al. , "The development of surgery for gastro-oesophageal reflux disease," *Surgery of the Oesophagus*, 233-245 (1988).
Jamieson, et al., "Laparoscopic Nissen Fundoplication," *Annals of Surgery*, 220:137-145 (1994).
Janssen, et al., " Prospective randomized comparison of teres cardiopexy and Nissen fundoplication in the surgical therapy of gastro-oesophageal reflux disease," *Br. J.Surg.* 80:875-878 (1993).
Jennings, et al., "A Novel Endoscopic Transgastric Fundoplication Procedure for Gastroesophageal Reflux: An Initial Animal Evaluation," *Journal of Laparoendoscopic Surgery*, 2:207-213 (1992).
Kahrilas, "Gastroesophageal Reflux Disease,"*JAMA*, 276:983-988 (1996).
Kraemer, M.D., et al., "Laparoscopic Hill repair," *Gastrointestinal Endoscopy*, 40:155-159 (1994).
Little, M.D., "Mechanisms of Action of Antireflux Surgery: Theory and Fact," *World Journal of Surgery*, 16:320-325 (1992).
Mason, et al., "Nissen Fundoplication Prevents Shortening of the Sphincter During Gastric Distention," *Arch Surg.*, 132:719-726 (1997).
McGouran, M.D., et al., "A laser-induced scar at the cardia increases the yield pressure of the lower esophageal sphincter," *Gastronintestinal Endoscopy*, 36:439-443 (1990).
McKernan, "Laparoscopic repair of gastroesophageal reflux disease," *Surgical Endoscopy*, 8:851-856 (1994).
Nathanson, et al., "Laparoscopic Ligamentum teres (round ligament) cardiopexy," *Br. J. Surg.*, 78:947-951 (1991).
Nissen, "Eine einfache Operation zur Beeinflussung der Refluxoesophagitis," *Journal Suisee De Medecine*, 590-592 (1956).
O'Connor, et al., "Endoscopic placement of collagen at the lower esophageal sphincter to inhibit gastroesophageal reflux: a pilot study of 10 medically intractable patients," *Gastrointestinal Endoscopy*, 34:106-112 (1988).
Pedinielli, "Traitement Chirurgical de la Herinie Hiatale Par La Technique du Collet", *Ann. Chir.*, 18:1461-1474 (1964). (English Abstract).
Polk, et al. "Hiatol Hernia and Esophagitis: A survey of indications for operation and technic and results of fundoplication," *Ann. Surg.*, 173:775-781 (1971).
Rampal, et al., "Technique Chirurgicale, Traitement des hernies hiatales et du reflux aesophagien par la cardio-pexie avec le ligament round de foie," *La Presse Medicale*, 75:617-619 (1967).
Rich, "Simple GERD Treatment Offers New Alternative,"(www.medicalpost.com website), Mar. 1999.
Singh, et al., "Evaluation of the Endoscopic Suturing System in the Treatment of GERD," *DDW*, May 16-19, 1999.
Skinner, et al., "Surgical management of esophageal reflux and hiatus hernia," *Journal of Thoracic and Cardiovascular Surgery*, 53:33-54 (1967).
Starling, et al. Assessment of the Angelchik Prosthesis for Treatment of Symptomatic Esophageal Reflux, *World J. Surg.* 11, 350-355 (1987).
Tocornal, M.D., et al., "A musosol flap valve mechanism to prevent gastroesophageal reflux and esophagitis," *Surgery*, 64:519-523 (1968).
Wang, et al., "A new anti-flux procedure: cardiac oblique invagination," *Chung Hua Wai Ko Tsa Chih*, Feb; 33 (2) 73-5 (1995). (English Abstract).
Watson, et al., "Comparison of anterior, posterior and total fundoplication using a viscera model," *Diseases of the Esophagus*, 10: 110-114 (1997).
Westbrook, et al., "Posterior Surgical Approaches to the Rectum," *Annals of Surgery*, 195:677-691 (1982).
International Search Report dated Oct. 16, 2000.
Contractor QQ et al., Endoscopic esophagitis and gastroesophageal flap valve. *J Clin Gastroenterol* Apr. 1999;28(3):233-7.
Donahue PE et al., Endoscopic control of gastro-esophageal reflux: status report. *World J Surg* Mar.-Apr. 1992:16(2):343-6.
Donahue PE et al., Endoscopic sclerosis of the gastric cardia for prevention of experimental gastroesophageal reflux. *Gastrointest Endosc* May-Jun. 1990;36(3):253-6.
Hill LD and Kozarek RA. The gastroesophageal flap valve. *J Clin Gastroenterol* Apr. 1999:28(3):194-7.

Hill LD et al., Antireflux surgery. A surgeon's look. *Gastroenterol Clin. Nort Am* Sep. 1990:19(3):745-75.

Hill LD et al., The gastroesophageal flap valve: in vitro and in vivo observations. *Gastrointest Endosc* Nov. 1996:44(5):541-7.

Hill LD, Inraoperative measurement of lower esophageal sphincter pressure. *J Thorac Cardiovasc Surg* Mar. 1978:75(3):378-82.

Hill LD, Myths of the esophagus, *J Thorac Cardiovasc Surg* Jul. 1989:98(1):1-10.

Ismail T et al., Yield pressure. anatomy of the cardia and gastro-oesophageal reflux. *Br J Surg* Jul. 1995:82(7):943-7.

Jennings RW et al., A novel endoscopic transgastric fundoplication procedure for gastroesophageal reflux: an initial animal evaluation. *J Laparoendosc Surg* Oct. 1992;2(5):207-13.

Kadirkamanathan SS et al., Antireflux operations at flexible endoscopy using endoluminal stitching techniques: an experimental study. *Gastrointest Endosc* Aug. 1996;44(2):133-43.

Mason RJ et al., A new intraluminal antigastroesophageal reflux procedure in baboons. *Gastrointest Endosc* Mar. 1997;45(3):283-90.

McGouran RC and Galloway JM, A laser-induced scar at the cardia increases the yield pressure of the lower esophageal sphincter. *Gastrointest Endosc* Sep.-Oct. 1990;36(5):439-43.

McGouran RC et al., Does measurement of yield pressure at the cardia during endoscopy provide information on the function of the lower oesophageal sphincter mechanism? *Gut* Mar. 1988;29(3):275-8.

McGouran RC et al., Is yield pressure at the cardia increased by effective fundoplication? *Gut* Oct. 1989:30(10):1309-12.

O'Connor KW and Lehman GA. Endoscopic placement of collagen at the lower esophageal sphincter to inhibit gastroesophageal reflux: a pilot study of 10 medically intractable patients. *Gastrointest Endosc* Mar.-Apr. 1988;34(2):106-12.

Slim K et al., Intraoperative esophageal manometry and fundoplications: prospective study. *World J Surg* Jan. 1996:20(1):55-9.

Carvalho PJPC et al., Fibrosis of gastric cardia after endoscopic sclerosis. Mechanism for control of experimental reflux? *Am Surg* Mar. 1990;56(3):163-6.

Kadirkamanathan SS et al., An ambulant procine model of acid reflux used to evaluate endoscopic gastroplasty. *Gut* Jun. 1999;44(6):782-8.

O'Connor KW et al., An experimental endoscopic technique for reversing gastroesophageal reflux in dogs by injecting inert material in the distal esophagus. *Gastrointest Endosc* Oct. 1984;30(5):275-80.

Rupp TH and Lehman GA, Endoscopic antireflux techniques. Endoluminal and laparoscopic. *Gastrointest Endosc Clin N Am* Apr. 1994;4(2):353-68.

Shafik A, Intraesophageal Polytef injection for the treatment of reflux esophagitis. *Surg Endosc* Mar. 1996;10(3):329-31.

Thor KBA et al., Reappraisal of the flap valve mechanism in the gastroesophageal junction. A study of a new valvuloplasty procedure in cadavers. *Acta Chir Scand* Jan. 1987;153(1):25-8.

\* cited by examiner

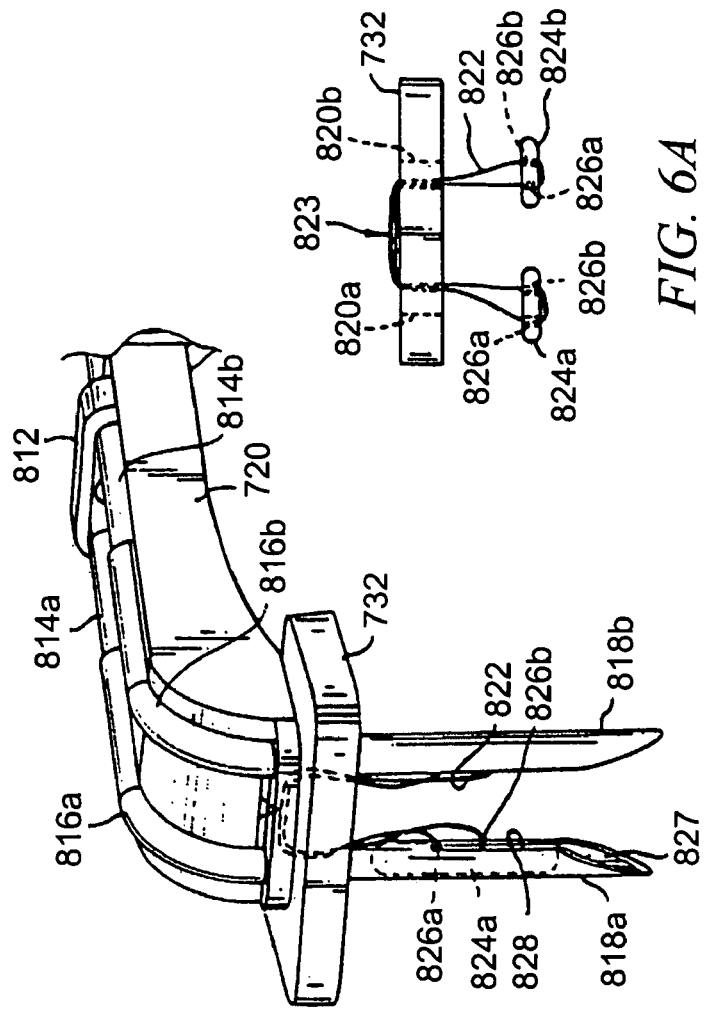
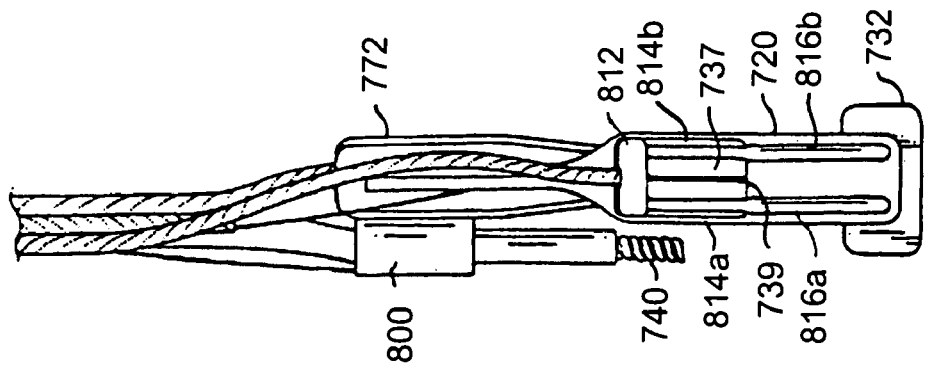
FIG. 6A
FIG. 6B
FIG. 5

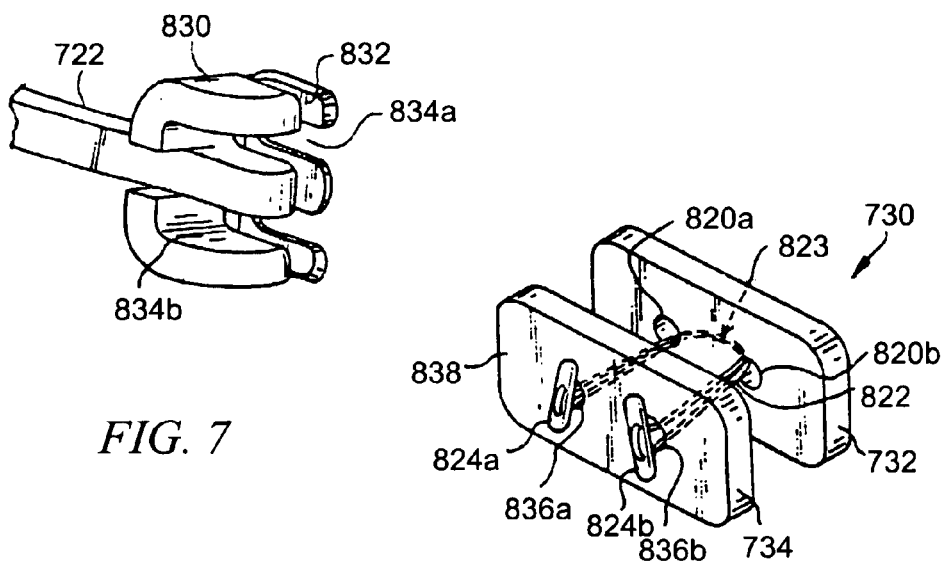
FIG. 7
FIG. 8
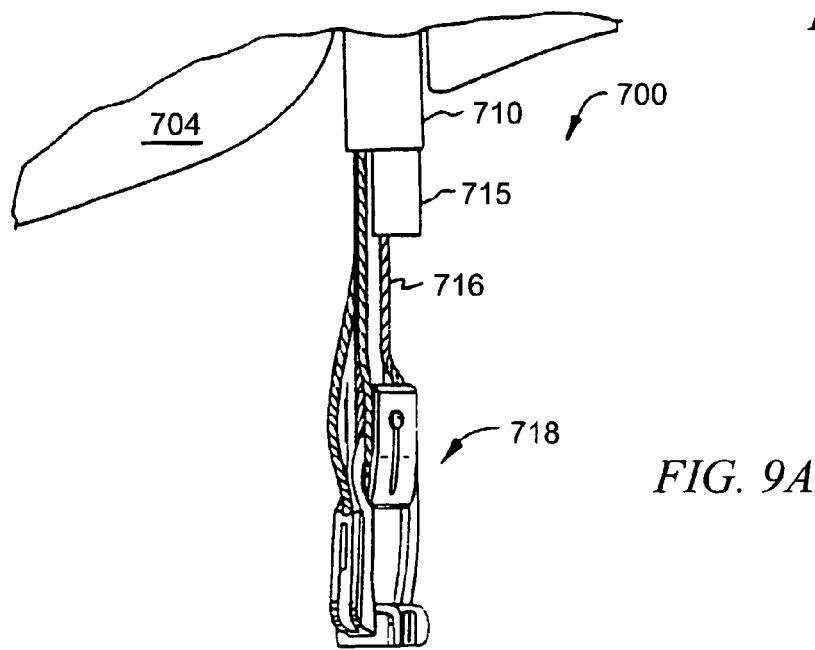
FIG. 9A

TISSUE RECONFIGURATION

This application is a continuation of application U.S. Ser. No. 09/574,424, filed May 19, 2000, now U.S. Pat. No. 6,494,888 entitled TISSUE RECONFIGURATION, which is a continuation-in-part of application U.S. Ser. No. 09/520, 273, filed Mar. 7, 2000, now U.S. Pat. No. 6,663,639 entitled METHODS AND DEVICES FOR TISSUE RECONFIGURATION, and application U.S. Ser. No. 09/519,945, filed Mar. 7, 2000, now U.S. Pat. No. 6,506,196 entitled DEVICE AND METHOD FOR CORRECTION OF A PAINFUL BODY DEFECT, both of which claim priority from provisional application U.S. Ser. No. 60/140,492, filed Jun. 22, 1999, entitled STOMACH ELEVATOR METHOD AND DEVICE, all hereby incorporated by reference.

BACKGROUND

This invention relates to methods and apparatus for reconfiguring tissue, and more particularly to reconfiguring tissue in the vicinity of the gastroesophageal junction.

Gastroesophageal reflux disease (GERD) is a common upper-gastrointestinal disorder in which acidic contents of the stomach flow inappropriately from the stomach into the esophagus. Backflow of gastric contents into the esophagus results when gastric pressure is sufficient to overcome the resistance to flow that normally exists at the gastroesophageal junction (GEJ) or when gravity acting on the contents is sufficient to cause flow through the GEJ. Medication, open surgical procedures, minimally invasive surgical techniques, and endoscopic techniques are known for treating GERD.

SUMMARY

According to one aspect of the invention, an apparatus includes an elongated member configured for transoral placement into the stomach, and a distal end effector including first and second members configured to engage stomach tissue, e.g., stomach tissue beyond the esophageal junction. The first and second members are movable relatively toward one another generally in a first plane, and the distal end effector is movable relative to the elongated member in a second plane generally transverse to the first plane.

Embodiments of this aspect of the invention may include one or more of the following features.

The distal end effector includes a third member configured to engage stomach tissue. The third member is movable in a distal direction relative to the first and second members. The third member includes a tissue engaging portion, e.g., a coil having a tissue penetrating tip.

The apparatus includes a tissue securement member for coupling to at least one of the first and second members for securing together tissue engaged thereby. The tissue securement member includes a first part for coupling to the first member for engagement with a first tissue section, a second part for coupling to the second member for engagement with a second tissue section to be secured to the first tissue section, a suture attached to the first part, and a securing element attached to the suture and configured for engagement with the second part when the first and second members are moved relatively toward one another to engage the first and second tissue sections, thereby to secure the second part to the first part. The securing element is configured for deployment from the first member, and the first member includes a deploying element for deploying the securing element from the first member. The first member includes tissue piercing elements defining a channel for receiving securing elements.

The second plane is generally perpendicular to the first plane. The distal end effector is configured for movement between a first position generally aligned with the elongated member and a second position in which the distal end effector has moved in the second plane out of alignment with the elongated member. A cable actuatable from a proximal end of the apparatus and coupled to the distal end effector moves the distal end effector in the second plane. A cable actuatable from the proximal end of the apparatus and coupled to the distal end effector moves the first and second members generally in the first plane.

The elongated member defines a channel for receiving an endoscope.

According to another aspect of the invention, a method includes advancing an apparatus including an elongated member transorally into the stomach. The apparatus includes a distal end effector having first and second members configured to engage stomach tissue. The first and second members are movable relatively toward one another generally in a first plane. The method includes then moving the distal end effector relative to the elongated member in a second plane generally perpendicular to the first plane to position the first and second members for engagement with the tissue.

Embodiments of this aspect of the invention may include one or more of the following features.

The first and second members are moved relatively toward one another in the first plane to engage tissue, e.g., stomach tissue beyond the esophageal junction. Moving the first and second members engages a first tissue section with a first securing part and a second tissue section with a second securing part. The first securing part includes a suture attached thereto and a securing element attached to the suture. The method includes moving the securing element into engagement with the second securing part to secure the second securing part to the first securing part. Moving the first and second members causes tissue piercing elements of the first member to pierce tissue. Securing elements are deployed through the tissue piercing elements.

The method further includes piercing the tissue with a third member of the distal end effector prior to engaging the tissue with the first and second members.

The instrument and method of the invention advantageously provide an endoscopic approach to treating GERD that does not require the surgical formation of portals to access the GEJ. The procedure can be performed as an outpatient procedure done under sedation, without general anesthesia being required. The procedure can be performed by gastroenterologists rather than a surgeon, and takes less time, has fewer complications and side-effects and has lower overall procedure costs than surgical methods. The procedure recreates or augments the natural anatomy, and is easily reversible.

Other features, objects, and advantages of the invention will be apparent from the following detailed description, and from the claims.

DESCRIPTION OF DRAWINGS

FIG. 5 is a side view of the distal end of the instrument, turned 90 degrees relative to FIG. 4A;

FIG. 6A is an illustration of a first part of the tissue fixation device of FIG. 2;

FIG. 6B is an illustration of the first jaw member with the first part of the tissue fixation device mounted to the jaw member;

FIG. 7 is an illustration of the second jaw member;

FIG. 8 is an illustration of the tissue fixation device of FIG. 2;

FIGS. 9A–9F show the instrument of FIG. 1 in use; and

DETAILED DESCRIPTION

Figure 1:
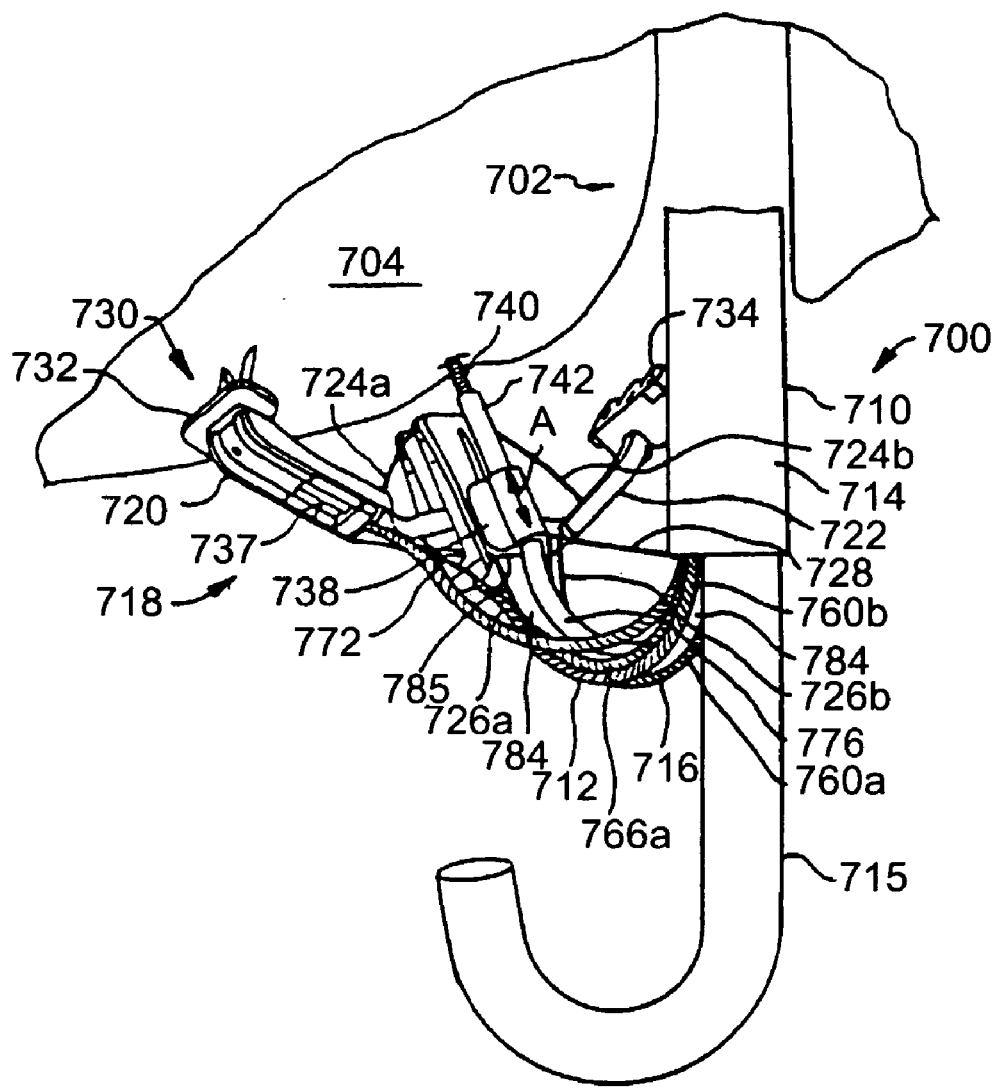
FIG. 1 is a diagrammatic representation of an instrument in use to reconfigure tissue in the vicinity of the gastroesophageal junction of the stomach.

Referring to FIG. 1, an instrument 700 for reconfiguring stomach tissue, e.g., stomach tissue in the vicinity of the gastroesophageal junction (GEJ) 702, such as tissue 704 of the lesser curvature of the stomach, is shown. The GEJ is the region of transition from the esophagus and the stomach. The lesser curvature of the stomach is a portion of the stomach located beyond the GEJ. Instrument 700 includes an elongated shaft 710 dimensioned to permit transoral access to the stomach, and a tissue manipulator 712 for manipulating stomach tissue. Positioned within a lumen 714 defined by shaft 710 is a standard GI endoscope 715 providing visual guidance of the reconfiguring procedure. Instrument 700 is particularly adapted for treating GERD. Using instrument 700, as described below, a bulge, plication or tissue wrap is formed in the vicinity of gastroesophageal junction 702 to reduce reflux of stomach fluids into the esophagus.

Figures 2, 3A:
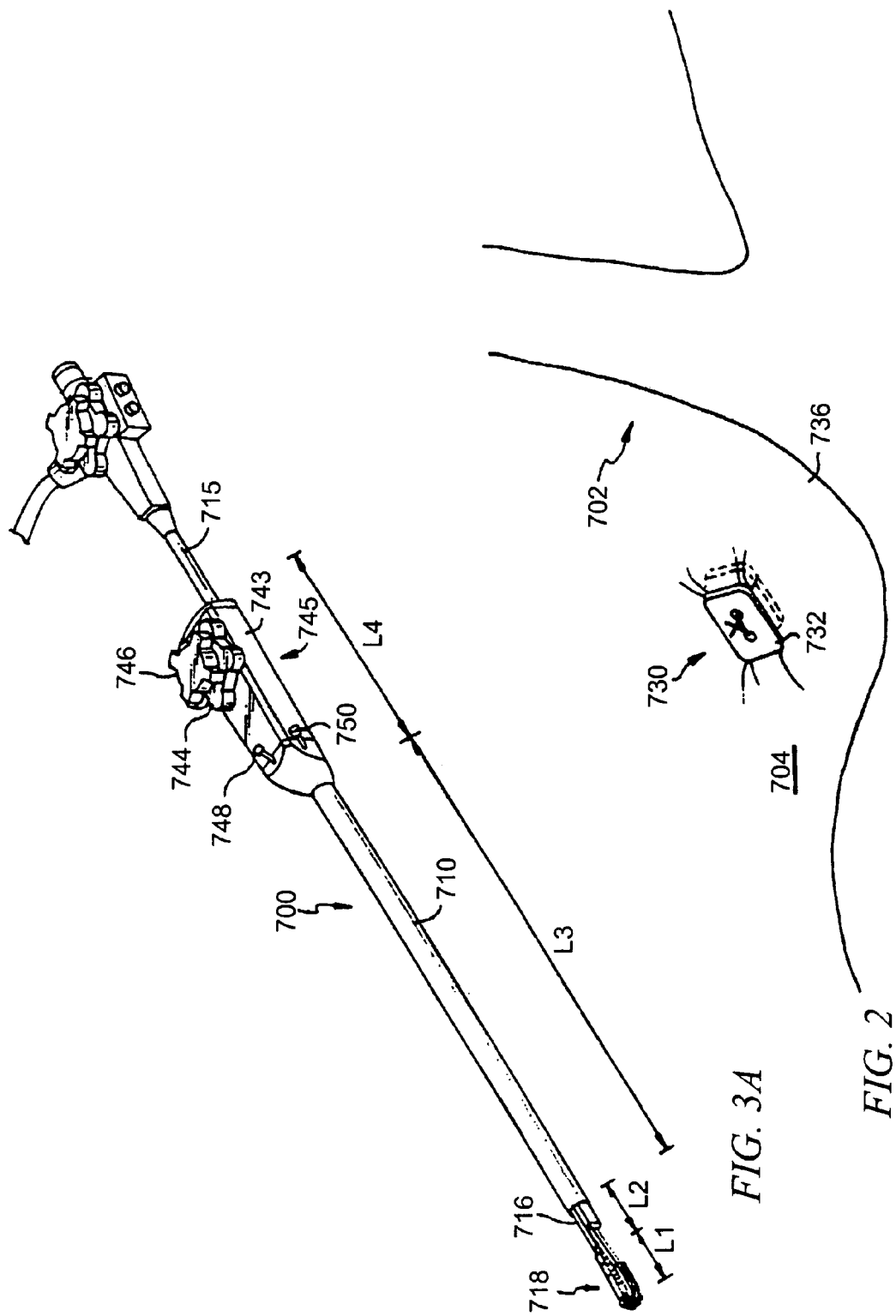
FIG. 2 shows a tissue fixation device deployed by the instrument of FIG. 1 in use to secure a bulge formed in the tissue.
FIG. 3A is an illustration of the instrument of FIG. 1.

Tissue manipulator 712 has an elongated cable assembly 716 housed within lumen 714 of shaft 710, and a distal end effector 718 actuated to perform the various steps in the tissue reconfiguring procedure by cable assembly 716. End effector 718 includes first and second jaw members 720, 722 which engage tissue 704. Cable assembly 716 includes first and second cable pairs 724a, 724b, and 726a, 726b for moving jaws 720, 722 relatively toward and away from one another, respectively, in a first plane, and a third cable 728 for moving end effector 718 relative to shaft 710 in a second plane generally transverse to, and preferably perpendicular to, the first plane, as described further below. During insertion into the stomach, end effector 718 is aligned with shaft 710 (as shown in FIG. 3A). Once positioned in the stomach, cable 728 is actuated to articulate end effector 718 out of alignment with shaft 710 (as shown in FIG. 1).

Cable assembly 716 includes a spring beam 784, formed from, e.g., stainless steel, extending into shaft 710. End effector 718 is attached to beam 784 at a distal end 785 of beam 784. Beam 784, in its rest state, is biased toward a straight alignment. Pulling cable 728 bends beam 784. When cable 728 is released, beam 784 returns toward the straight alignment.

Referring also to FIG. 2, mounted to first jaw 720 is a first part 732 of a tissue securement member, e.g., a fixation device 730, and mounted to second jaw 722 is a second part 734 of tissue fixation device 730. As described further below, after jaws 720, 722 engage tissue 704 and manipulate the tissue in a wrapping action to create a bulge 736 in, e.g., the lesser curvature of the stomach, tissue fixation device 730 is deployed to secure the engaged tissue together. Cable assembly 716 includes a fourth cable 737 for deploying fixation device 730, as described further below.

End effector 718 further includes a tube 738 and a third tissue engaging member, e.g., a coil 740, received within tube 738, for purposes described below. Coil 740 is housed within an overtube 742, and coil 740 and overtube 742 can be moved axially proximally and distally relative to jaws 720, 722, along the axis, A, of cable assembly 716. Coil 740 can be rotatably advanced into tissue.

Figure 3B:
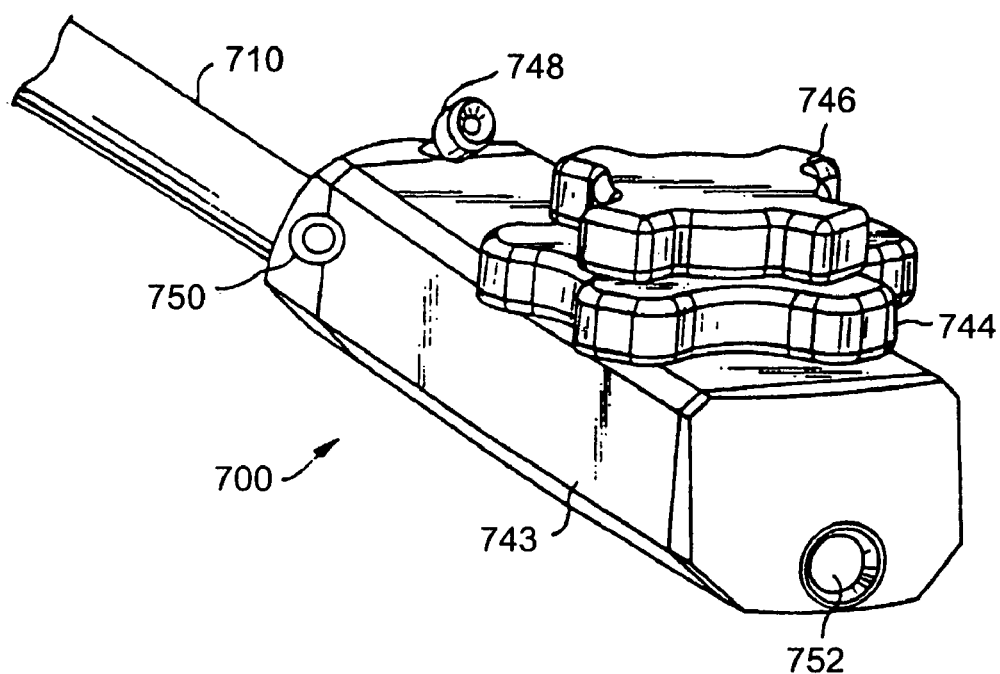
FIG. 3B shows a proximal end of the instrument.

Referring to FIG. 3A, instrument 700 has, at its proximal end 745, a handle 743 with a control knob 744 for controlling cables 724a, 724b, 726a, 726b to close and open jaws 720, 722, and a control knob 746 for controlling cable 728 to move end effector 718. Handle 743 includes a port 748 through which coil 740 and overtube 742 can be introduced into shaft lumen 714, and a pull-knob 750 for deploying tissue fixation device 730, as described below. As shown in FIG. 3B, handle 743 defines a channel 752 through which endoscope 715 is introduced into shaft lumen 714.

Figure 3C:
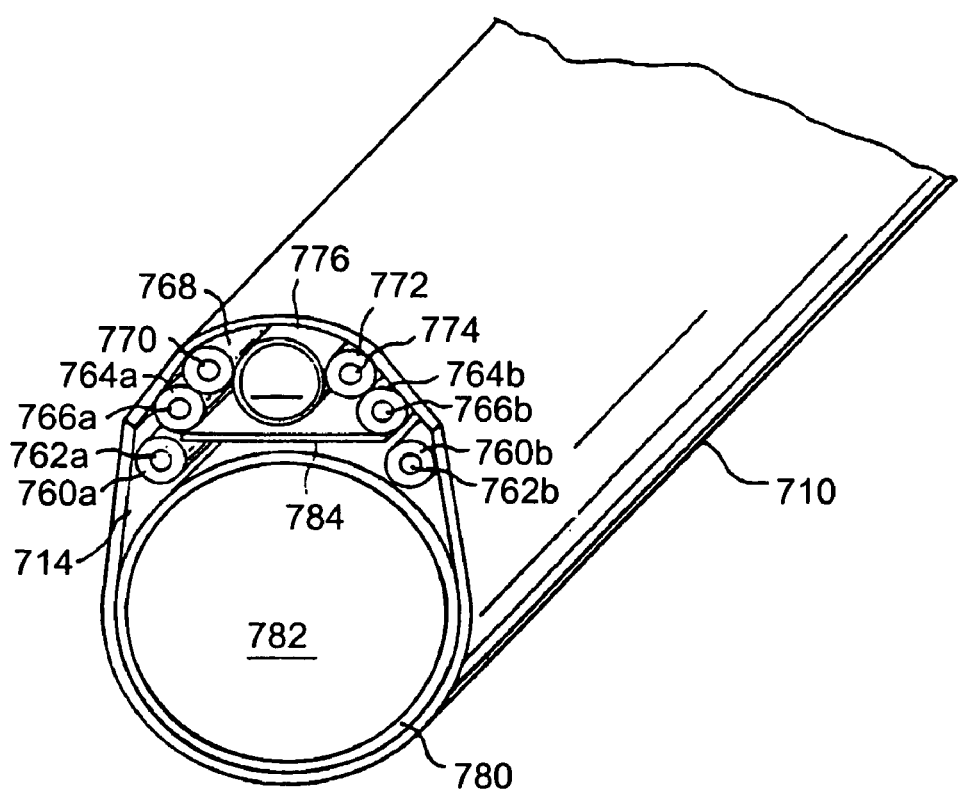
FIG. 3C shows the working channels in a shaft of the instrument.
Figure 3D:
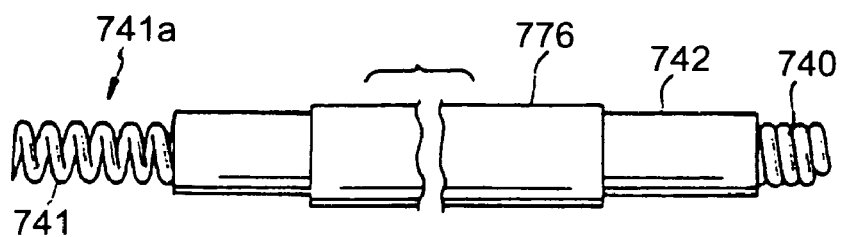
FIG. 3D is an illustration of a coil assembly of the instrument.

Referring to FIGS. 1 and 3C, which shows the working channels in shaft 710 for receiving the various cables, overtube 742 and endoscope 715, within lumen 714 of shaft 710 are cable housings 760a, 760b defining channels 762a, 762b in which cables 724a, 724b for closing jaws 720, 722 are received, and cable housings 764a, 764b defining channels 766a, 766b in which cables 726a, 726b for opening jaws 720, 722 are received. Within lumen 714 are also a cable housing 768 defining a channel 770 in which cable 728 for bending end effector 718 is received, and a cable housing 772 defining a channel 774 in which cable 737 for deploying fixation device 730 is received. Coil 740 and overtube 742 are received in a channel 778 defined in a coil housing 776 in lumen 714. Housing 776 extends from port 748 to tube 738. As shown in FIG. 3D, coil 740 has a tissue penetrating tip 741 and a distal section 740a having a looser wound coil than the remainder of coil 740. Endoscope 715 is received in a channel 782 defined in an endoscope housing 780 in lumen 715.

Spring beam 784 is located generally between cable housing 776 and endoscope housing 780, and extends about 4 inches into shaft 710 from the distal end of the shaft where beam 784 is mounted to shaft 710 by, e.g., silicone adhesive/sealant. The various cable housings and spring beam 784 do not move relative to shaft 710 and handle 743. It is the movement of the cables within the cable housings that actuate end effector 718. Shaft 710 is preferably formed from, e.g., heat-shrink tubing.

Referring again to FIG. 3A, end effector 718 has a length, L1, of about 2 inches, cable assembly 716 extends axially by a length, L2, of about 2.5 inches from shaft 710, shaft 710 has a length, L3, of about 23.5 inches, and handle 743 has a length, L4, of about 5 inches. Cable assembly 716, spring beam 784, and shaft 710 have the necessary flexibility to permit transoral placement of instrument 700 into the stomach. The length, L1, of relatively rigid end effector 718 is minimized to ensure the necessary flexibility of instrument 700 is maintained. The distance that cable assembly 716 extends axially from shaft 710 is selected to cantilever beam 784 permitting the desired bending of end effector 718 relative to shaft 710 to position jaws 720, 722 against the inner surface of the stomach in the vicinity of the GEJ.

Distal end effector 718 is sized to fit through a 12–16 mm diameter channel (corresponding to the diameter of the esophagus) and shaft 710 has an outer diameter of about 12 to 16 mm to enable transoral passage of instrument 700 into the stomach. Scope channel 782 has a diameter of either about 8 mm or 10 mm. An 8 mm diameter scope channel allows passage of 7.9 mm pediatric gastroscope, and a 10 mm diameter scope channel allows passage of a 9.8 mm adult gastroscope. Channel 778 has a diameter of about 2–3 mm for receiving cable 742.

Figure 4A:
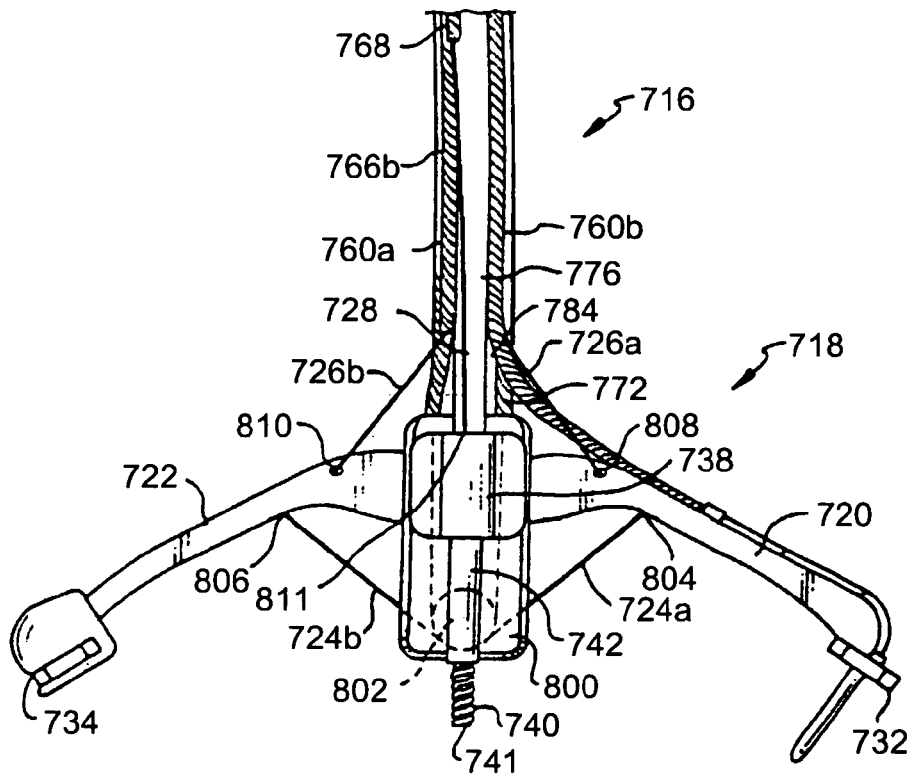
FIG. 4A is a top view of a distal end of the instrument, shown with first and second jaw members in an open position.
Figure 4B:
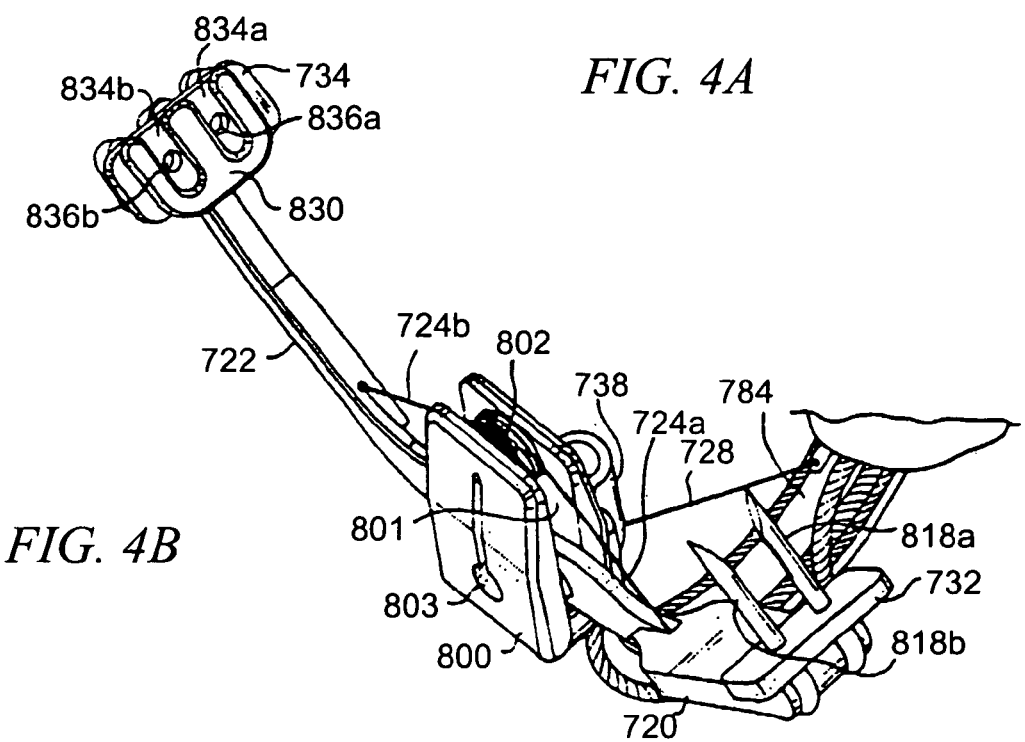
FIG. 4B shows the distal end of the instrument located off-axis relative to a shaft of the instrument.

Distal end effector 718 is shown in more detail in FIGS. 4A and 4B. End effector 718 includes a central mount 800 defining a slot 801. Spanning slot 801 and supported by mount 800 is a pin 803 to which 720, 722 are pivotally mounted. Central mount 800 also houses two pulleys 802 over which cables 724a, 724b are respectively passed for closing jaws 720, 722. Cables 724a, 724b terminate at points 804, 806 on jaws 720, 722, respectively. Cables 726a, 726b for opening jaws 720, 722 terminate at points 808, 810 on jaws 720, 722, respectively, proximal of points 804, 806. Tube 738 of end effector 718 for receiving coil 740 and overtube 742 is attached to mount 800, and cable 728 for bending end effector 718 terminates at point 811 on tube 738.

Pulling cables 724a, 724b proximally moves jaws 720, 722 toward one another generally in a first plane (in the plane of the paper in FIG. 4A). Pulling cables 726a, 726b proximally moves jaws 720, 722 away from one another generally in the first plane. Pulling cable 728 proximally bends beam 784 moving end effector 718 in a second plane (out of the plane of the paper in FIG. 4A) generally perpendicular to the first plane.

Referring also to FIG. 5, jaw 720 includes two guide tubes 816a, 816b and a slider 812 including two push rods 814a, 814b guided within tubes 816a, 816b, respectively. Slider 812 is mounted to jaw 720 to slide relative to jaw 720. Tubes 816a, 816b curve about jaw 720 to terminate in tissue penetrating tips 818a, 818b (FIG. 6B), respectively. Push rods 814a, 814b can be formed from molded plastic such as polyethylene or polypropylene or as a braided stainless steel cable to provide the flexibility to follow the curve of tubes 816a, 816b. Cable housing 772 is attached to slider 812 and cable 737 terminates at a fixed point 739 on jaw 720. Actuation of cable 737 pushes slider 812 distally, as described below.

First part 732 of tissue fixation device 730 is shown in more detail in FIGS. 6A and 6B. First part 732 of tissue fixation device 730 defines through holes 820a, 820b (FIG. 6A), and part 732 is loaded onto jaw 720 with tips 818a, 818b received in through holes 820a, 820b, respectively. Connected to part 732 with a suture 822 are two securing elements, e.g., bars 824a, 824b. Each bar 824a, 824b defines two through holes 826a, 826b. Suture 822 is threaded through holes 826a, 826b of the bars and through holes 820a, 820b of part 732, and is tied together forming a knot 823 to secure bars 824a, 824b to part 732. Tubes 818a, 818b each define a channel 827 for receiving one of bars 824a, 824b, and a slot 828 communicating with channel 827 for receiving suture 822 therethrough.

Referring particularly to FIGS. 4B and 7, jaw 722 has a distal member 830 defining a slot 832 for receiving second part 734 of fixation device 730, and slots 834a, 834b for receiving tissue penetrating tips 818a, 818b. Second part 734 of fixation device 730 defines through holes 836a, 836b for receiving tips 818a, 818b. When jaws 720, 722 are closed, tips 818a, 818b pass through slots 834a, 834b and holes 836a, 836b. Actuation of fixation device deployment cable 737 after closing jaws 720, 722 pushes slider 812 and push rods 814a, 814b distally, advancing bars 824a, 824b out of tissue penetrating tips 818a, 818b, and locating t-bars 824a, 824b on the far side 838 of second part 734 of fixation device 730, as shown in FIG. 8.

Figure 9C:
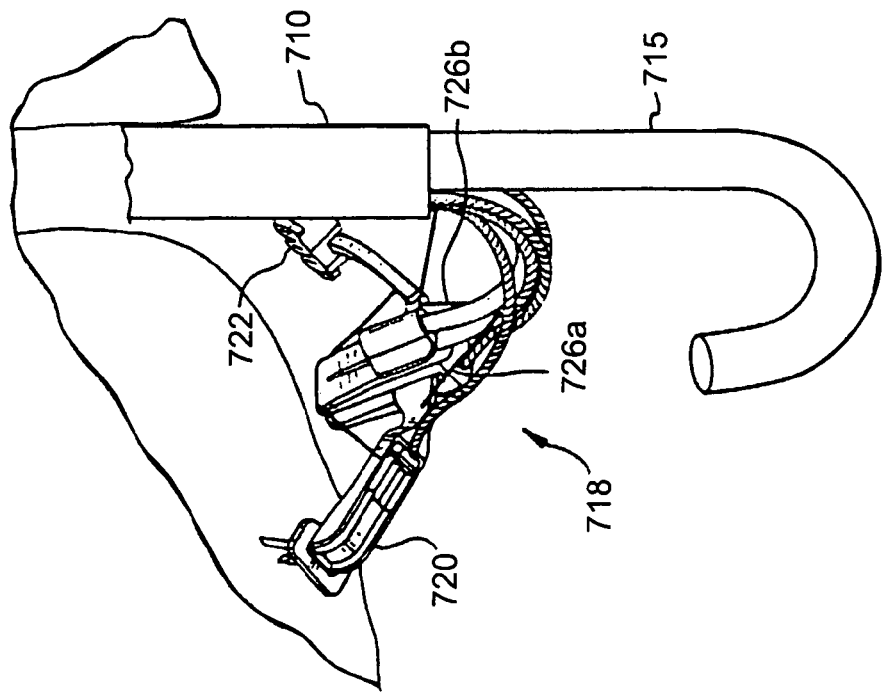
Figure 9B:
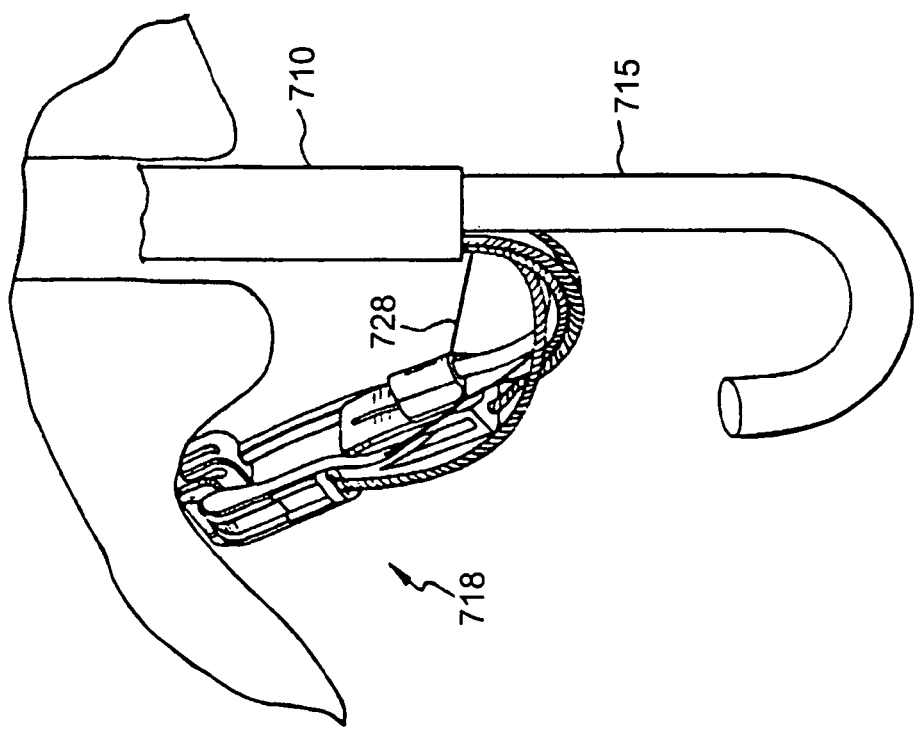

Referring to FIGS. 9A–9F, in use, under endoscopic guidance, the physician advances instrument 700 transorally to position end effector 718 in the stomach. During advancement into the stomach, end effector 718 is generally aligned along the axis of shaft 710, as shown in FIG. 9A. The physician then turns control knob 746 to pull cable 728 proximally, thereby bending beam 784 moving end effector 718 out of alignment with shaft 710 to the position shown in FIG. 9B. By then turning control knob 744 to pull cables 726a, 726b, jaws 720, 722 are pivoted about pins 803 to the open position shown in FIG. 9C.

Figure 9E:
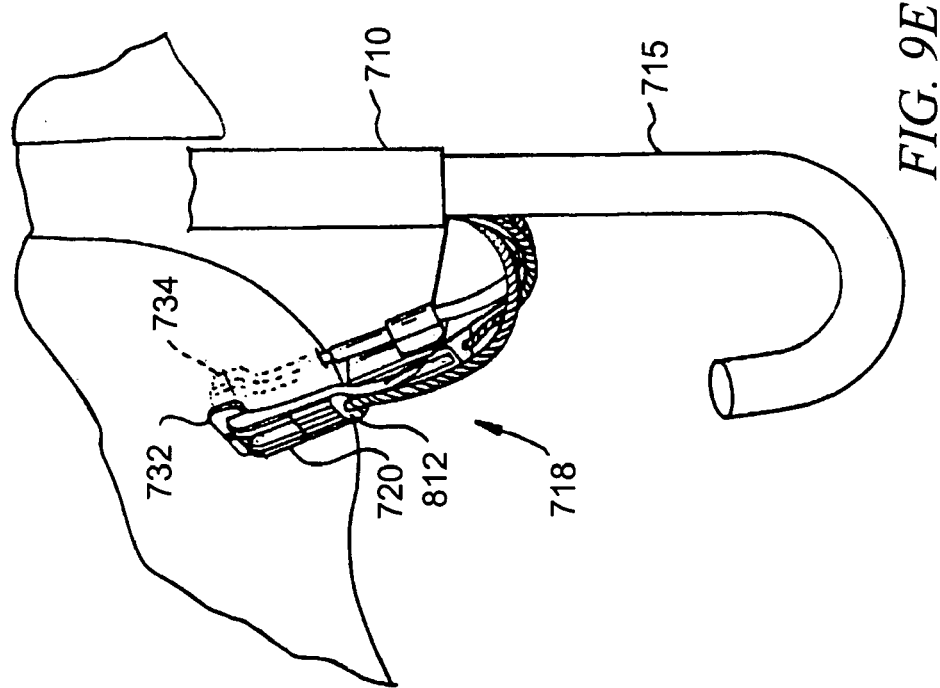
Figure 9D:
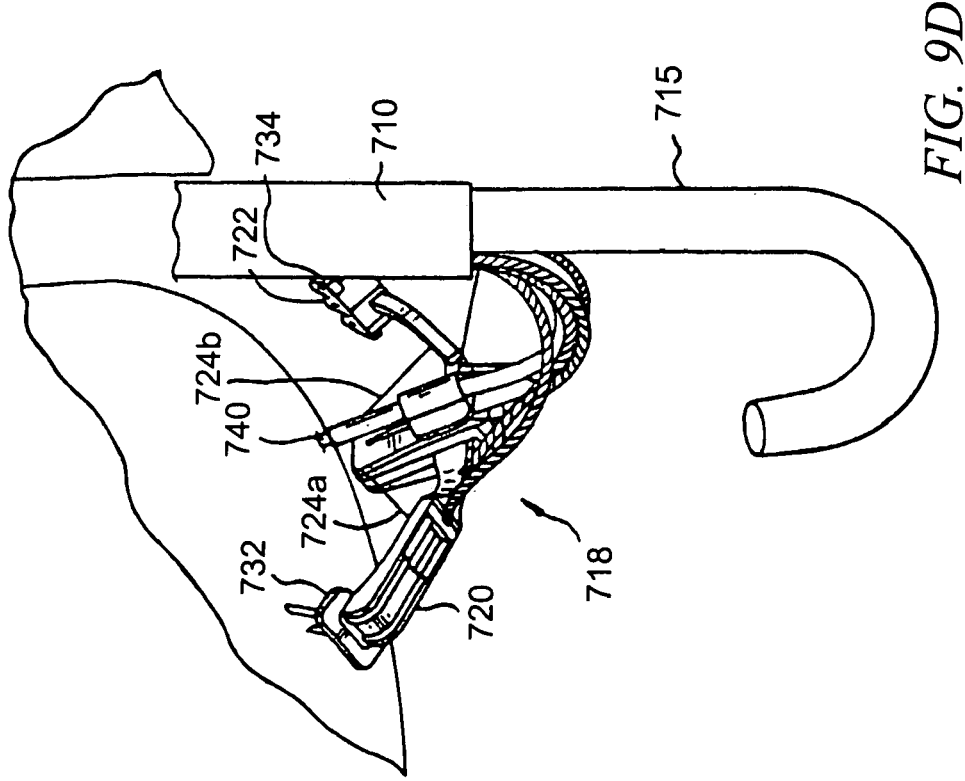

The physician then advances coil 740 and overtube 742 by pushing the coil and overtube distally in channel 778 advancing coil 740 and overtube 742 out of tube 738 and into contact with stomach tissue, preferably stomach tissue beyond the gastroesophageal junction, as shown in FIG. 1. With overtube 742 pressing against the tissue to stabilize the tissue, the physician rotates coil 740 while applying slight distal pressure to advance the coil into the tissue, as shown in FIG. 9D. Coil 740 and overtube 742 are then pulled proximally to pull tissue between jaws 720, 722. Jaws 720, 722 are then closed by turning control knob 744 to pull cables 724a, 724b proximally, as shown in FIG. 9E. The turning of the control knob can also be the action that pulls coil 740 and overtube 742 proximally, ensuring that coil 740 and overtube 742 are positioned out of the way of the closing of the jaws. A lockout can be incorporated to prevent the jaws from closing if coil 740 and overtube 742 are not in their proximal position.

Figure 9F:
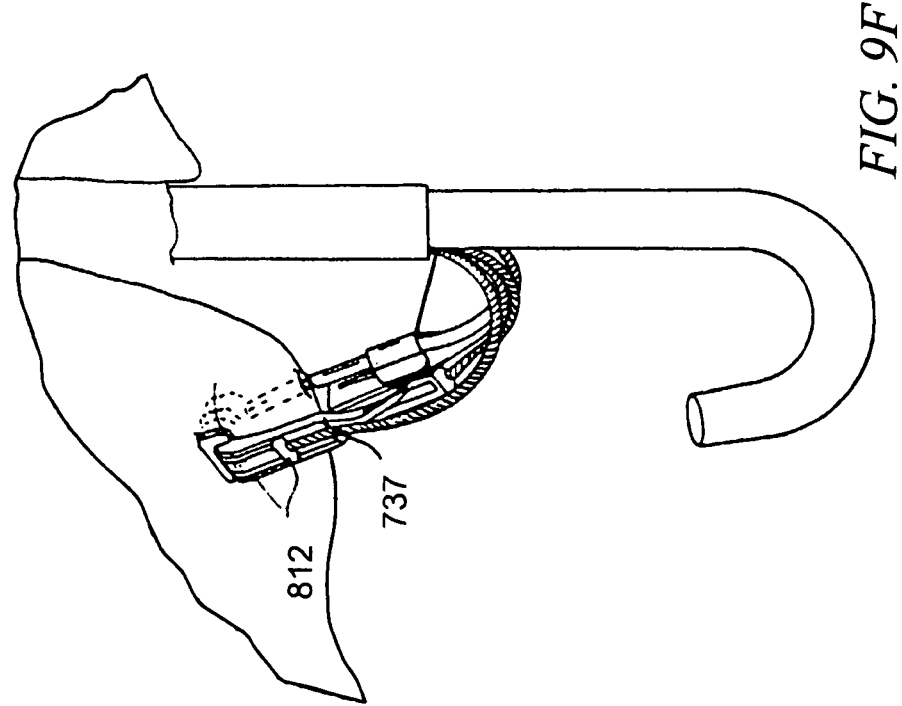

The closing of the jaws places parts 732, 734 of fixation device 730 in contact with two tissue sections, e.g., against two spaced tissue surfaces in the stomach, and causes tissue penetrating tips 818a, 818b to penetrate through the tissue and into holes 836a, 836b in second part 734 of fixation device 730. To deploy fixation device 730, the physician pulls cable 737 proximally removing slack from cable 737. Because cable housing 772 is of fixed length and is non-movably attached to the handle, removing slack from cable 737 causes cable housing 772 to move distally, advancing slider 812 to push t-bars 824a, 824b out of tissue penetrating tips 818a, 818b, as shown in FIG. 9F.

Figure 10:
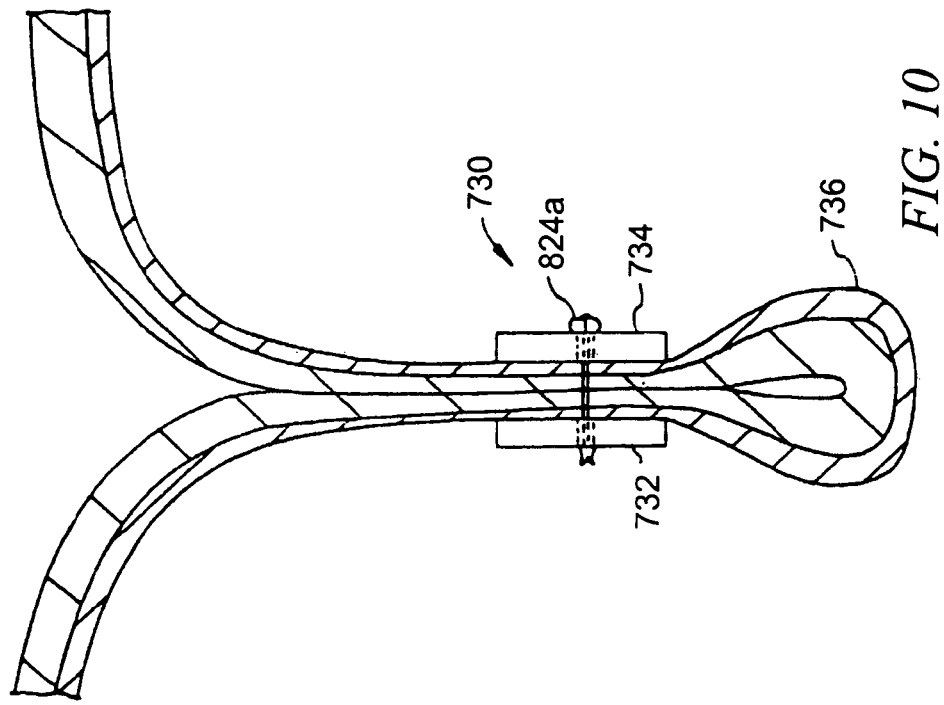
FIG. 10 is an illustration of tissue secured with the tissue fixation device of FIG. 2.

The physician then opens the jaws, disengages jaw 722 from second part 734, returns the distal end effector to its original position generally aligned with shaft 710, closes the jaws and removes instrument 700. FIG. 10 shows a cross-section of the tissue with fixation device 730 in place securing bulge 736.

Other embodiments are within the scope of the following claims.

For example, rather than a coil 740, alternative tissue penetrating or grasping elements such as a T-bar suture or two small grasping jaws can be employed. Instrument 700 can be used without the third tissue engaging member.

What is claimed is:

1. Apparatus comprising:
   an elongated member configured for transoral placement into a stomach;
   a distal end effector including first and second members configured to engage stomach tissue, the first and second members being movable relatively toward one another generally in a first plane, the distal end effector being movable relative to the elongated member in a second plane generally transverse to the first plane such that the distal end effector is retroflexed out of alignment with the elongated member; and a tissue piercing element coupled with the first member:

wherein the distal end effector further includes a third member configured to engage stomach tissue, the third member being movable in a distal direction relative to the first and second members, wherein the third member includes a tissue engaging portion, the tissue engaging portion comprising a coil having a tissue penetrating tip.

2. Apparatus comprising:

an elongated member configured for transoral placement into a stomach;

a distal end effector including first and second members configured to engage stomach tissue, the first and second members being movable relatively toward one another generally in a first plane, the distal end effector being movable relative to the elongated member in a second plane generally transverse to the first plane such that the distal end effector is retroflexed out of alignment with the elongated member;

a tissue piercing element coupled with the first member; and a tissue securement member for coupling to at least one of the first and second members for securing together tissue engaged thereby;

wherein the tissue securement member comprises a first part for coupling to the first member for engagement with a first tissue section, a second part for coupling to the second member for engagement with a second tissue section to be secured to the first tissue section, a suture attached to the first part, and a securing element attached to the suture and configured for engagement with the second part when the first and second members are moved relatively toward one another to engage the first and second tissue sections, thereby to secure the second part to the first part.

3. The apparatus of claim 2 wherein the securing element is configured for deployment from the first member.

4. The apparatus of claim 2 wherein the first member includes a deploying element for deploying the securing element from the first member.

5. Apparatus comprising:

an elongated member configured for transoral placement into a stomach;

a distal end effector including first and second members configured to engage stomach tissue, the first and second members being movable relatively toward one another generally in a first plane, the distal end effector being movable relative to the elongated member in a second plane generally transverse to the first plane such that the distal end effector is retroflexed out of alignment with the elongated member; and a tissue piercing element coupled with the first member, wherein the tissue piercing element defines a channel for receiving a securing element.

6. Apparatus comprising:

an elongated member configured for transoral placement into a stomach;

a distal end effector including first and second members configured to engage stomach tissue, the first and second members being movable relatively toward one another generally in a first plane, the distal end effector being movable relative to the elongated member in a second plane generally transverse to the first plane such that the distal end effector is retroflexed out of alignment with the elongated member; and a tissue piercing element coupled with the first member; wherein the first member includes a second tissue piercing element.

7. The apparatus of claim 6 wherein the second tissue piercing element defines a channel for receiving a securing element.

8. A method comprising:

advancing an apparatus including an elongated member transorally into the stomach, the apparatus including a distal end effector having first and second members configured to engage stomach tissue, the first and second members being movable relatively toward one another generally in a first plane;

moving the distal end effector relative to the elongated member in a second plane generally transverse to the first plane such that the distal end effector is retroflexed out of alignment with the elongated member to position the first and second members for engagement with the tissue;

piercing tissue with a tissue piercing element associated with the first member; and engaging tissue by moving the first and second members relatively toward one another generally in the first plane;

wherein the moving of the first and second members engages a first tissue section with a first securing part and a second tissue section with a second securing part, the method further comprising moving a securing element of the first securing part into engagement with the second securing part to secure the second securing part to the first securing part.

9. The method of claim 8 further comprising deploying the securing element through the tissue piercing element.

10. The method of claim 8 wherein the moving of the first and second members causes first and second tissue piercing elements of the first member to pierce tissue, the method further comprising deploying first and second elements of the securing element each through one of the first and second tissue piercing elements.

11. A method comprising:

advancing an apparatus including an elongated member transorally into the stomach, the apparatus including a distal end effector having first and second members configured to engage stomach tissue, the first and second members being movable relatively toward one another generally in a first plane;

moving the distal end effector relative to the elongated member in a second plane generally transverse to the first plane such that the distal end effector is retroflexed out of alignment with the elongated member to position the first and second members for engagement with the tissue;

piercing tissue with a tissue piercing element associated with the first member; and piercing the tissue with a third member of the distal end effector prior to engaging the tissue with the first and second members.

12. A method of treatment, comprising:

engaging a plurality of regions of stomach tissue with a plurality of members from within the stomach;

moving the plurality of members relatively toward one another to pinch the plurality of regions of engaged stomach tissue together thereby reconfiguring tissue in a vicinity of a gastroesophageal junction; and securing the engaged plurality of regions of stomach tissue together by deploying two securing elements connected by suture through the engaged plurality of regions of stomach tissue.

13. A method of treatment, comprising:

engaging a plurality of regions of tissue with a plurality of members from within the stomach;

moving the plurality of members relatively toward one another to wrap tissue in a vicinity of a gastroesophageal junction around the gastroesophageal junction; and securing the engaged plurality of regions of tissue together by deploying two securing elements connected by suture through the engaged plurality of regions of tissue.

14. A method of treatment, comprising:

engaging a plurality of regions of tissue with a plurality of members from within the stomach;

moving the plurality of members relatively toward one another to pinch the plurality of regions of engaged tissue together in a non-intussuscepting manner thereby reconfiguring tissue in a vicinity of a gastroesophageal junction; and securing the engaged plurality of regions of tissue together by deploying two securing elements connected by suture through the engaged plurality of regions of tissue.

15. A method of treatment, comprising:

engaging a plurality of regions of tissue with a plurality of members from within the stomach;

moving the plurality of members relatively toward one another to circumferentially relative to a circumference of a gastroesophageal junction to pinch the plurality of regions of engaged tissue together thereby reconfiguring tissue in a vicinity of the gastroesophageal junction; and securing the engaged plurality of regions of tissue together by deploying two securing elements connected by suture through the engaged plurality of regions of tissue.

16. A method of reconfiguring tissue in the vicinity of a junction between first and second hollow organs, comprising:

engaging a plurality of regions of tissue of the first organ with a plurality of members from within the first organ;

moving the plurality of members relatively toward one another to pinch the plurality of regions of engaged tissue of the first organ together thereby reconfiguring tissue in a vicinity of the junction; and securing the engaged plurality of regions of tissue together by deploying two securing elements connected by suture through the engaged plurality of regions of tissue.

* * * * *